United States Patent [19]

Jasin et al.

[11] Patent Number: 4,952,501

[45] Date of Patent: Aug. 28, 1990

[54] METHOD FOR ANALYZING AND SYNTHESIZING FUNCTIONAL POLYPEPTIDE SEQUENCES FOR ASSEMBLY INTO ENHANCED OR MULTI-FUNCTIONAL PROTEINS

[75] Inventors: Maria Jasin, Ft. Lauderdale, Fla.; Paul R. Schimmel, Lexington, Mass.

[73] Assignee: Massachusetts Institute of Technology, Cambridge, Mass.

[21] Appl. No.: 188,133

[22] Filed: Apr. 26, 1988

[51] Int. Cl.$^5$ .................... C12P 21/00; C12P 19/34; C12N 15/00; C12N 1/20

[52] U.S. Cl. .................................. 435/69.2; 435/91; 435/172.3; 435/252.33; 435/320; 935/11; 935/14; 935/29; 935/73; 935/80; 935/82

[58] Field of Search .................... 435/69.2, 91, 172.3, 435/252.33, 320; 935/11, 14, 29, 73, 80, 82

[56] References Cited

PUBLICATIONS

Merrill et al., *Molec. and Cell. Biol.*, 4(9): 1769–1776, 1984 (Sep.).
Ream et al., *Plasmid*, 10: 101–110, 1983.
Mock et al., *J. of Bacteriol.*, 159(2): 658–662, 1984 (Aug.).
Lehninger, *Principles of Biochemistry*, (Worth Publishers, Inc., New York, New York, 1982), pp. 180–185.
Mock et al., *J. of Bacteriol.*, 159(2): 658–662, 1984 (Aug.).
"Limited Proteolytic Digestion of Lac Repressor by Trypsin", by Files et al., *J. Biol. Chem.*, 251: 3386–3391 (1976).
"Purification and Properties of Alanine tRNA Synthetase from Escherichia Coli", by Putney et al., *J. Biol. Chem.*, 256: 198–204 (1981).
"Genetic Studies of the lac Repressor", by Coulondre et al., *J. Mol. Biol.*, 117: 525–567 (1977).
"Modular Arrangement of Functional Domains Along the Sequence of an Aminoacyl tRNA Synthetase", by Jasin et al, *Nature*, 306: 441–447 (Dec. 1983).
"Dispensable Pieces of an Aminoacyl tRNA Synthetase Which Activate the Catalytic Site", by Jasin et al., *Cell*, 36: 1089–1095 (Apr. 1984).
"Mutuants That Make More lac Repressor", by B. Muller-Hill et al., *Proc. Nat. Acad. Sci.*, 59: 1259–1264 (1968).
"Isolation of a Set of Hyrid lac Repressors Made in Vitro Between Normal lac Repressor and Its Homogeneous Tryptic Core", by N. Geisler et al., *Proc. Nat. Acad. Sci.*, 73: 3103–3106 (1976).

(List continued on next page.)

Primary Examiner—Thomas Mays
Attorney, Agent, or Firm—Kilpatrick & Cody

[57] ABSTRACT

Disclosed is a method for identifying and isolating gene sequences coding for polypeptide sequences which result in specific functional activities or phenotypes, which may then be synthesized and assembled to form new proteins. The assembled protein may contain only amino acid sequences essential for specific functions, have a new quaternary structure resulting from addition of an amino acid sequence with oligomeric activity, or exhibit multiple activities. Also disclosed is a method for identifying, analyzing and synthesizing amino acid sequences with oligomeric activity which may be used to enhance or add a new activity to a protein.

In one embodiment, the piece with oligomeric activity is fused onto a polypeptide with one or more additional activities. In another embodiment, this polypeptide sequence is hybridized with a second polypeptide consisting only of the sequence with oligomeric activity. In a variation of this second method, the first polypeptide may naturally contain a sequence with oligomeric activity and the second polypeptide sequence may be synthesized to complement the naturally occurring sequence. The protein-to-protein interactions serve to stabilize or enhance the activities on the first polypeptide sequences. These methods provide means for enhancing activity in sequences that occur naturally or in sequences which are synthesized from a variety of sources. The coupling piece may be spatially remote from the active or functional domain and still be effective in producing a protein with enhanced or restored or stabilized activity.

16 Claims, 12 Drawing Sheets

OTHER PUBLICATIONS

"Sequence Change in the DNA from the lacI Gene Arising from an Amber Mutation", by Lillis, Dept. Chem., U. of Pennsylvania, pp. 568–575.

"Cloned Truncated recA Genes in *E. coli* I, Effect on Radiosensitivity and recA+ Dependent Processes", by S. G. Sedgwick et al., *Mol. Gen. Genet.*, 185: 93–98 (1982).

"Cloned Truncated recA Genes in *E. coli* II, Effects of Truncated Gene Products on in vivo recA+ Protein Activity", by G. T. Yarranton et al., *Mol. Gen. Genet.*, 185: 99–104 (1982).

"Alkylation and Identification of the Histidine Residues at the Active Site of Ribonuclease*", by A. M. Crestfield et al., *J. Biol. Chem.*, 238: 2413–2420 (1963), and *J. Biol. Chem.*, 238: 2421–2428 (1963).

"Genetic Mapping of the Regulator and Operator Genes of the Lac Operon", by J. Davies et al., J. Mol. Biol., 36: 413–417 (1968).

pMJ801

Progressive Removal of the C-terminal Coding Region of *alaS*

Construction of Deletion Plasmids Using Partial Restriction Digests

Oligomerization of Native and Truncated Ala-tRNA Synthetase

Table I

Properties of amino terminal fragments of Ala-tRNA synthetase

| Size of amino terminal alaS protein segment (No. amino acids) | Approximate amount synthesized from plasmid | Adenylate synthesis | Aminoacylation of tRNA^Ala (complementation in vivo of alaS5) | Oligomerization |
|---|---|---|---|---|
| $NH_3^+\underline{\quad 257\quad}CO_2^-$ | m | − | − | n.d. |
| $NH_3^+\underline{\quad 385\quad}CO_2^-$ | m | + | − | − |
| $NH_3^+\underline{\quad 404\quad}CO_2^-$ | l | + | − | − |
| $NH_3^+\underline{\quad 461\quad}CO_2^-$ | m | + | + | n.d. |
| $NH_3^+\underline{\quad 468\quad}CO_2^-$ | h | + | + | − |
| $NH_3^+\underline{\quad 502\quad}CO_2^-$ | m | + | + | − |
| $NH_3^+\underline{\quad 596\quad}CO_2^-$ | m | + | + | n.d. |
| $NH_3^+\underline{\quad 612\quad}CO_2^-$ | l | + | + | n.d. |
| $NH_3^+\underline{\quad 695\quad}CO_2^-$ | h | + | +/− | − |
| $NH_3^+\underline{\quad 699\quad}CO_2^-$ | h | + | + | − |
| $NH_3^+\underline{\quad 808\quad}CO_2^-$ | h | + | + | + |
| $NH_3^+\underline{\quad 852\quad}CO_2^-$ | m | + | + | + |
| $NH_3^+\underline{\quad 875\quad}CO_2^-$ (Native) | h | + | + | + |

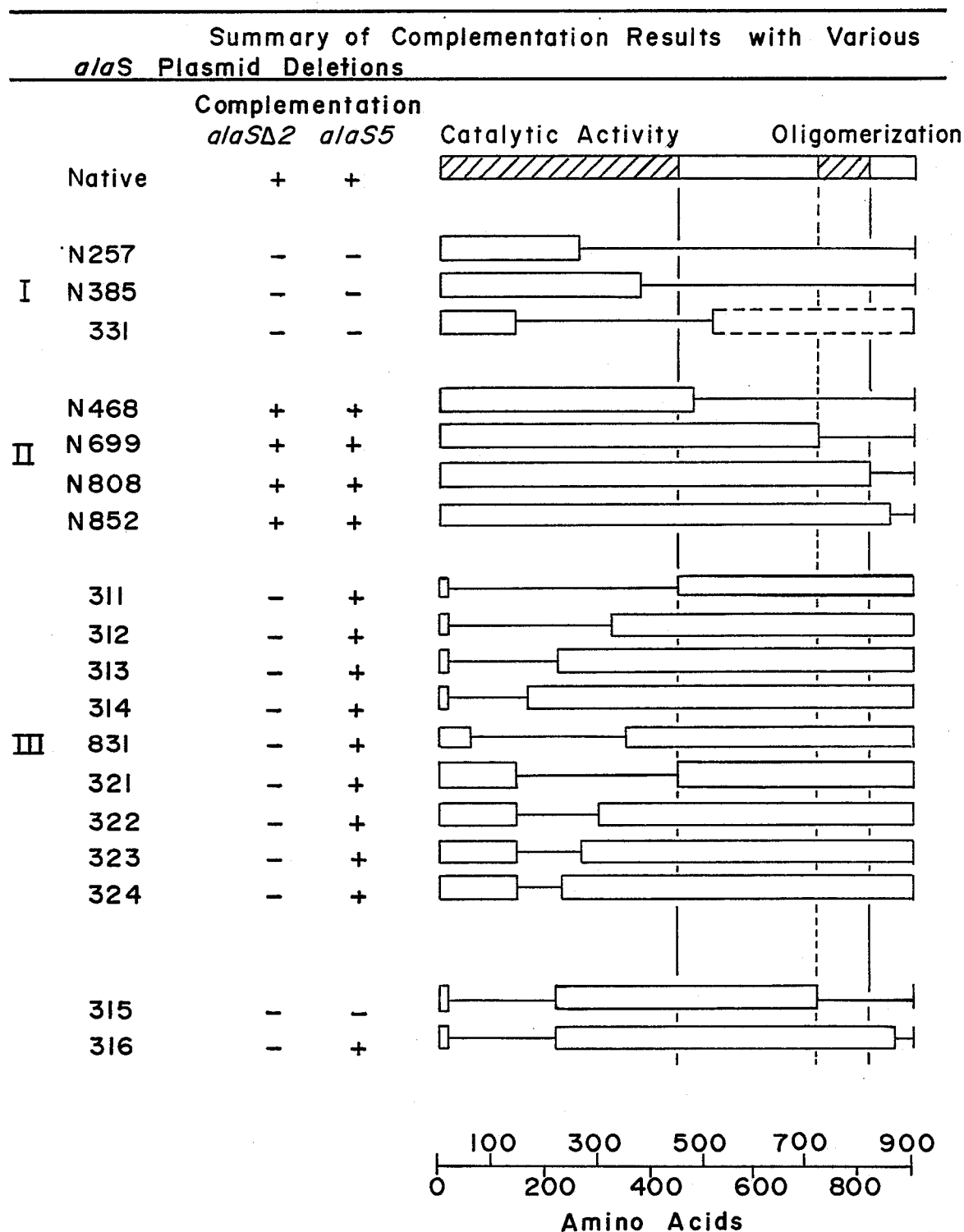

METHOD FOR ANALYZING AND SYNTHESIZING FUNCTIONAL POLYPEPTIDE SEQUENCES FOR ASSEMBLY INTO ENHANCED OR MULTI-FUNCTIONAL PROTEINS

The Government has rights in this invention pursuant to Grant Number NIH-2-R01-GM23562-06 awarded by the U.S. Department of Health and Human Services.

BACKGROUND OF THE INVENTION

Proteins are polymers of amino acids which have biological activity. Often a protein will possess several distinct activities. It would be advantageous to have a systematic approach for determining where the functional parts are located. These parts could then be synthesized from recombinant DNA plasmids and used as portable pieces which have a specific biological activity. A major advantage to the use of functional pieces is that they are often much smaller than the full sized protein from which they are extracted. This reduction in size is of great advantage in certain applications. For example, with small pieces it would be possible to join several together to produce a polyprotein with a set of functional activities in a combination that does not occur naturally. This kind of construction would probably be limited to sequences of 1,000 or fewer amino acids since this is the upper limit of naturally occurring polypeptide chains. Utilizing small pieces, the sizes of newly constructed polyproteins may be limited to those which may be handled by the appropriate cellular machinery. For example, DNA sequences encoding only the short functional pieces could be inserted into plasmids which are limited as to the number of nucleotides which may be incorporated.

Most previous work on mapping protein domains has relied on protease digestion of the native protein. These digestions can reduce the size of proteins, but it is almost impossible to control the point at which the digestion stops. Usually, a limited, stable fragment is obtained and the activity of this limited piece is tested. It is not possible to make internal deletions in a protein using a protease since the proteases act by digesting amino acid residues, and do not rejoin them to produce new polypeptide sequence arrangements.

In order for polypeptide sequences to be assembled to form the new protein, it must first be shown that the functional regions may be separated from the remainder of the protein and retain their functional activity. Secondly, a method for deleting specific portions of the protein must also be available. In addition, a means for reassembling the polypeptide sequences and expression of the protein must be available.

In considering the problem of assembly of the protein, it would be advantageous to be able to isolate and synthesize pieces with oligomerization activity for use in forming new quaternary structures. This may even further alter the functional activity of the protein.

A still further aspect of the formation of new protein molecules involves assembly of pieces which are themselves inactive but which have catalytic or other functional activity when joined together. In the general context of enzyme structure-function, two broad types of complementation or interactions have previously been observed. One, two variants of the same enzyme, each with a different modification or mutatation in the active site region, can interact and thereby restore activity. The classical studies of active site histidines in ribonuclease are an example, described by A. M. Crestfield, W. H. Stein, and S. Moore in *J. Biol. Chem.*, 238, 2413-2420 (1973 a) and *J. Bol. Chem.*, 238, 2421-2428 (1963). Two, mutant and wild-type polypeptides can associate to give inactive oligomers. There are classes of mutations that are dominant defective, as a result of formation of mixed-subunit tetramers between defective and wild-type proteins. Examples in the lacI and recA systems are described by Davis and Jacob in *J. Mol. Biol.* 36, 413-417 (1968), Mueller-Hill et al, *Proc. Nat. Acad. Sci. U.S.A.* 59, 1259-1264 (1968), Geisler and Weber, *Proc. Nat. Acad. Sci. U.S.A.* 73, 3103-3106 (1976), and Yarranton and Sedgwick in *Mol. Gen. Genet.* 185, 99-104 (1982).

It would be advantageous to have a method, such as one using readily synthesized, inactive polypeptide fragments, for reactivating the activity-deficient protein through a specific protein-protein contact that is well removed from the functional region. Such a method is not presently available.

It is therefore an object of the invention to provide a method for mapping multiple functional domains in a protein or polypeptide sequence.

Another object of the invention is to provide a method for creating hybrid polypeptides with one or more specific functional activities.

A still further object of the invention is to provide a method for making a nested set of overlapping deletions within the carboxyl terminal encoding portions of a gene for a specific protein so that the deleted gene may be inserted into recombinant DNA plasmids for transformation into an appropriate host strain and expression of the desired protein.

Another object of the invention is to provide a method for identifying, isolating and expressing nucleotide sequences which encode polypeptides with adhesive or coupling properties.

Yet another object of the invention is to map and isolate gene and amino acid sequences for the functional components of alanine-tRNA synthetase, specifically those for adenalate synthesis, transfer RNA interactions, and oligomerization.

SUMMARY OF THE INVENTION

The present invention is a method for identifying and isolating nucleotide sequences coding for polypeptides with specific functional activities. The polypeptides may then be synthesized by means of recombinant plasmids in an appropriate host strain for assembly into new proteins. The method includes means for determining functional activity of the synthesized fragments, distinguishing dispensable from indispensable (with respect to a particular activity or phenotype) sequences, and identifying the sequences with oligomeric or adhesive properties. These "portable" polypeptide fragments and the nucleotide sequences coding for them may be used to create polyproteins with enhanced or additional specific functional activities and altered quaternary structures, used in a host system for further production of one or more proteins, or used for further genetic engineering studies.

A specific example utilizing alanine-tRNA synthetase is disclosed. In this example, the nucleotide and amino acid sequences for the specific functional activities: adenylate synthesis, transfer RNA interactions, and oligomeric activity, are mapped. Further studies demonstrate how these pieces may be isolated and retain their functional activity, both in vivo or in vitro. Specific methods for making internal deletions within the dispensable or indispensable sequences and reassembling the sequences in recombinant plasmids are also taught. Additional uses for the adhesive or oligomeric portions are disclosed, such as in restoring activity of functionally inactive sequences by protein-protein interactions.

The methods disclosed in the example may be used with proteins or polypeptide sequences other than alanine-tRNA synthetase. Methods for excising or synthesizing the nucleotide sequences encoding polypeptides with one or more functions from a variety of sources are known to those skilled in the art. Recombinant plasmids may be utilized in the synthesis of "artificial" proteins or polypeptide sequences wherein the final product may have a variety of activities. These activities may be enhanced, or, indeed, made to operate when they are otherwise separated from the naturally occurring intact protein by "fusing" onto the polypeptide a sequence with oligomeric activity, such as the one isolated from alaninetRNA synthetase. The alanine-tRNA synthetase exemplifies a protein wherein several functional, distinct sequences are incorporated into the protein and whose activities are enhanced by hybridization with an additional segment with oligomeric activity.

Two embodiments of this method restore or enhance activity in polypeptides containing functional sequences. In the first method, the polypeptide is synthesized from a nucleotide sequence encoding both sequences with one or more desired activities or phenotypes and sequences with oligomeric activity. In the second method, a polypeptide is made which incorporates a sequence with oligomeric activity (either naturally or by genetic engineering) as well as one or more other functional activities which is then hybridized to a second sequence comprising at least the oligomeric activity. Other functional sequences may also be attached to the second oligomeric sequence.

BRIEF DESCRIPTION OF THE DRAWINGS

TABLE 1

Properties of amino terminal fragments of Ala-tRNA synthetase

Protein amounts were estimated from autoradiograms of SDS gels of maxicell extracts and, where possible, from measurements of ATP-PPi exchange activity. Maxicell synthesis is as described in FIG. 2.

Aminoacylation of tRNA Ala in vivo was checked by testing for complementation of the alaS5 chromosomal mutation. Plasmids were transformed into the temperature sensitive alaS5 strain KL380.

Figure 3:
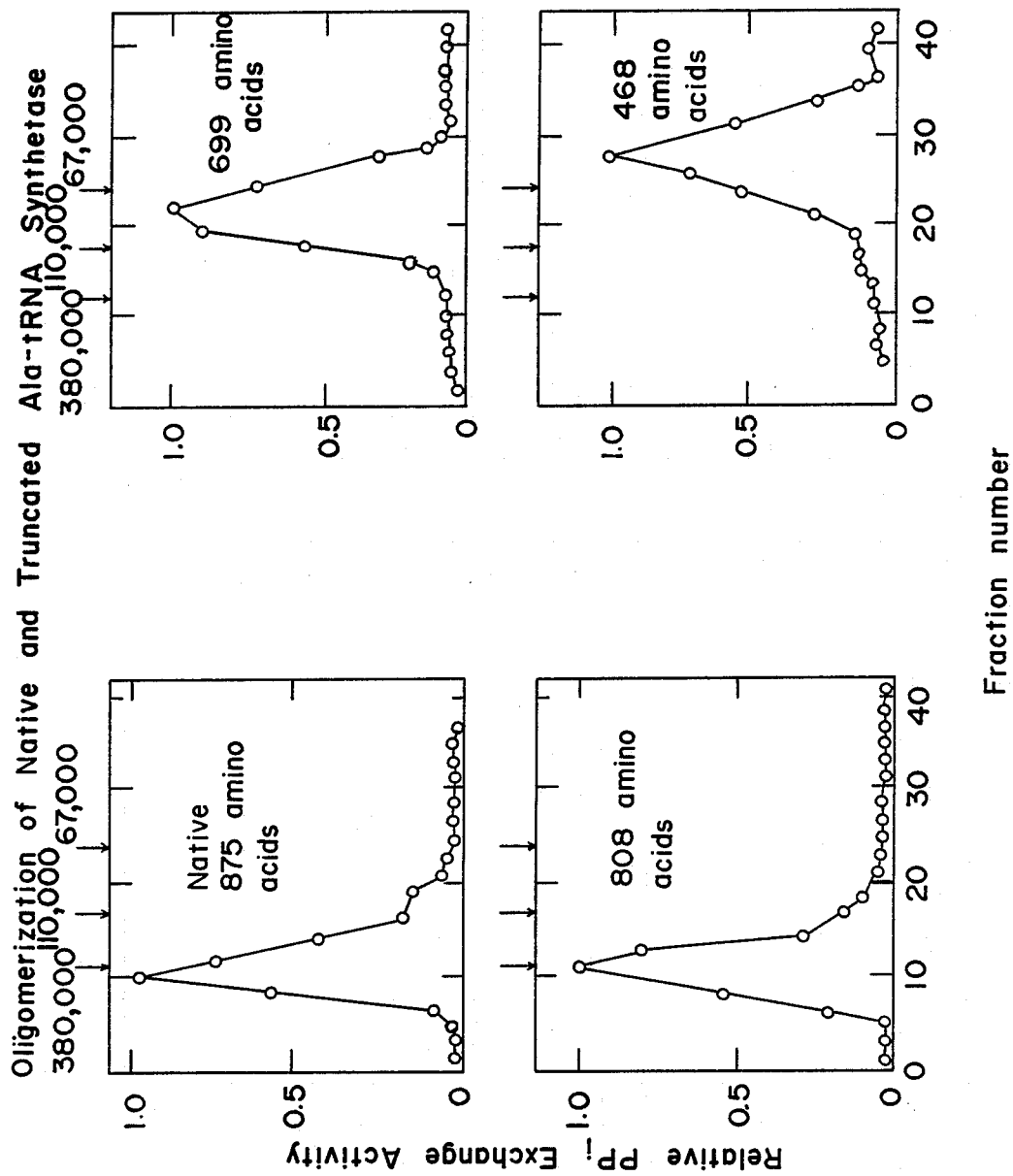

Oligomerization of truncated proteins was determined by molecular seive column chromatography, the results of which are shown in FIG. 3.

Symbols used: h (high: 8–10 fold amplification of alaS protein over levels produced by wild type strain which does not contain plasmid); m (moderate: 3–6 fold); l (low: less than 3-fold); + (the presence of an activity; − (the absence of an activity); N.D. (not determined).

TABLE 2

Summary of Complementation Results with Various alaS Plasmid Deletion.

Open bars: remaining in-frame coding regions;
solid lines: positions of gene deletions;
dashed bar: out-of-frame region.

Figure 1A:
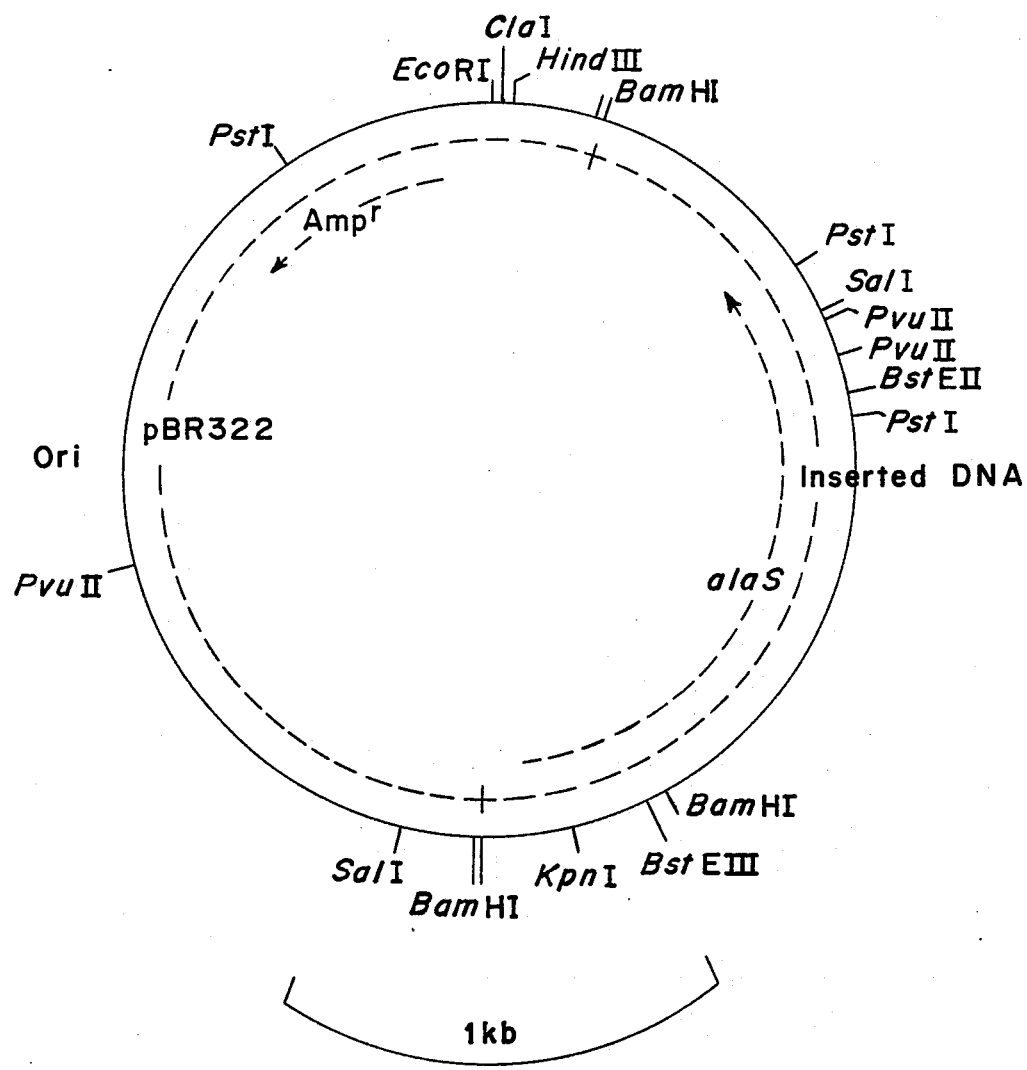

FIG. 1a is a restriction map of pMJ801. A 3.7 kb Sau3A1 fragment generated from a partial digest of pSP101 was cloned into the BamHI site of pBR322.

Figure 1B:
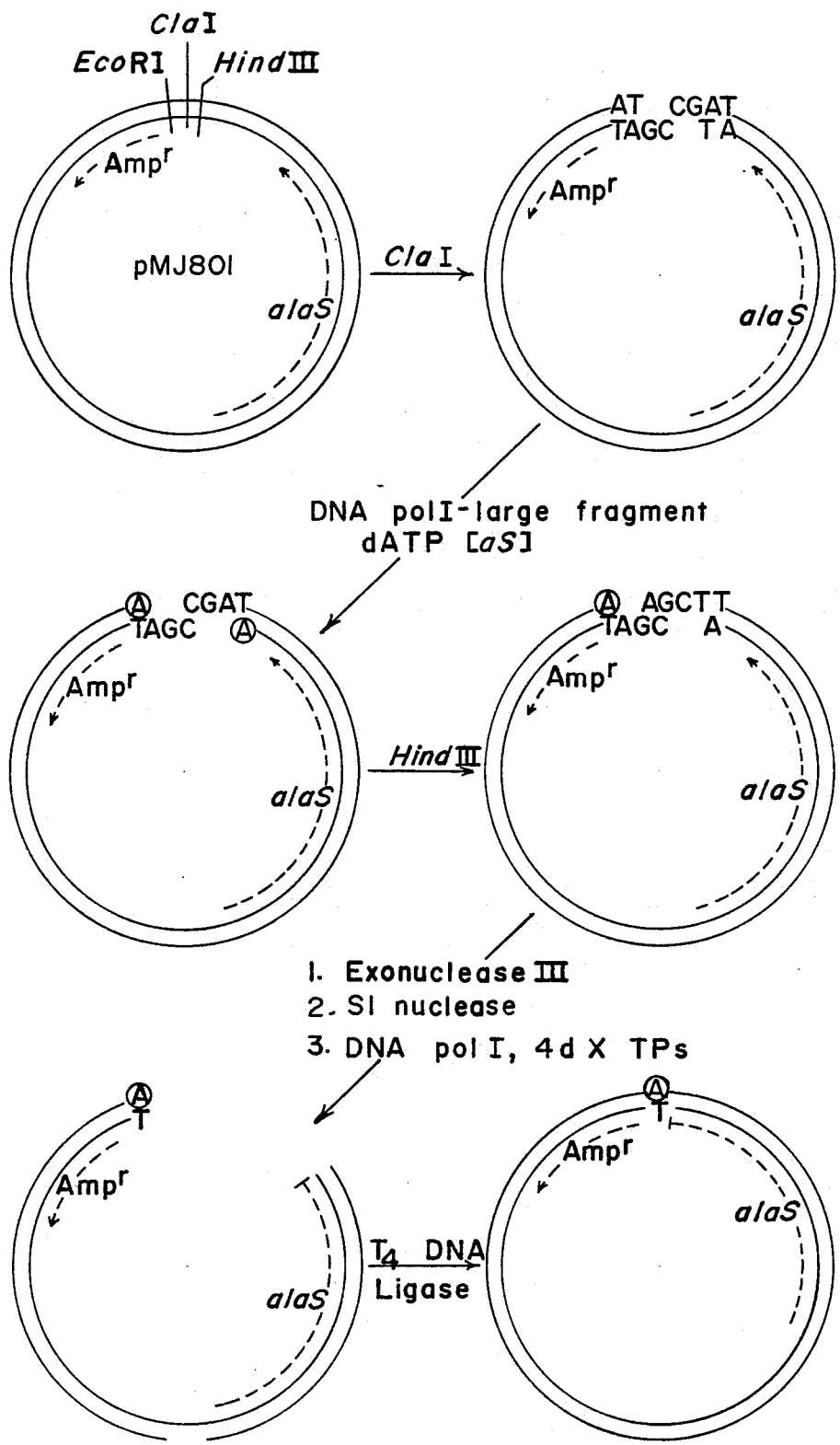

FIG. 1b is a schematic of the construction of deletions by progressive removal of the C-terminal coding region of alaS by asymmetric exonuclease III (exoIII) digestion.

Figure 1C:
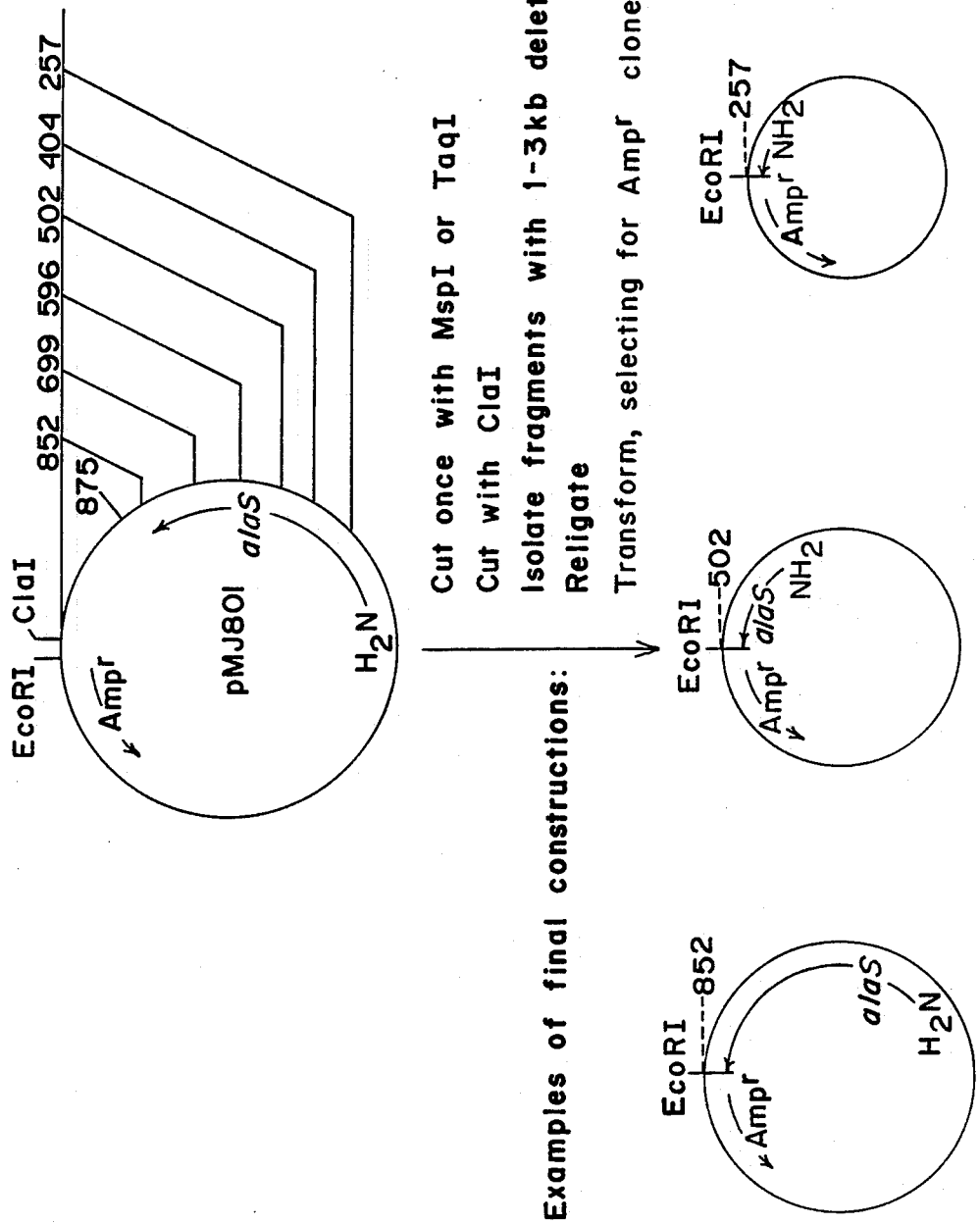

FIG. 1c is a schematic of the removal of defined portions of the C-terminal coding region of alaS by partial restriction enzyme digestion.

Figure 2:
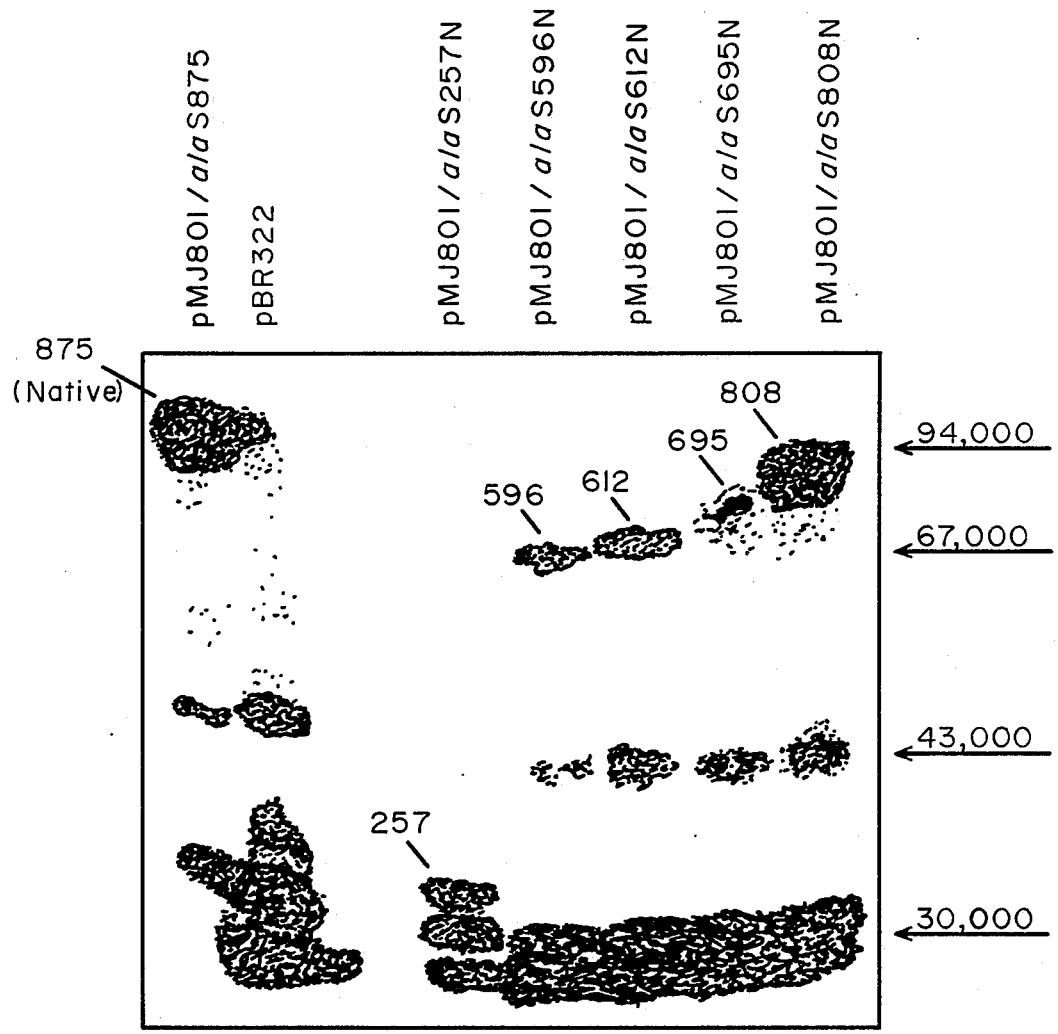

FIG. 2 is an autoradiogram of a 10% SDS-polyacrylamide gel of maxicell synthesized proteins from cells containing various deletion plasmids. Deletion plasmids were transformed into a met+ recA− strain (SG4051). Cells were UV-irradiated, incubated overnight with cycloserine, and protein synthesis was allowed to occur in the presence of [$^{35}$S] -methionine.

FIG. 3 graphs the column profiles of crude cell extracts containing the deletion plasmids. One mg of protein was run in KPO$_4$ (pH 7.5), 100 mM NaCl. 0.5 ml fractions were collected and assayed for alanine and valine ATP-PPi exchange activity. Only the amplified alanine dependent activity is shown. Peak valine activity is indicated by the arrow at 110,000. Molecular weight markers are phosphorylase A (380,000) and BSA (67,000).

Figure 4:
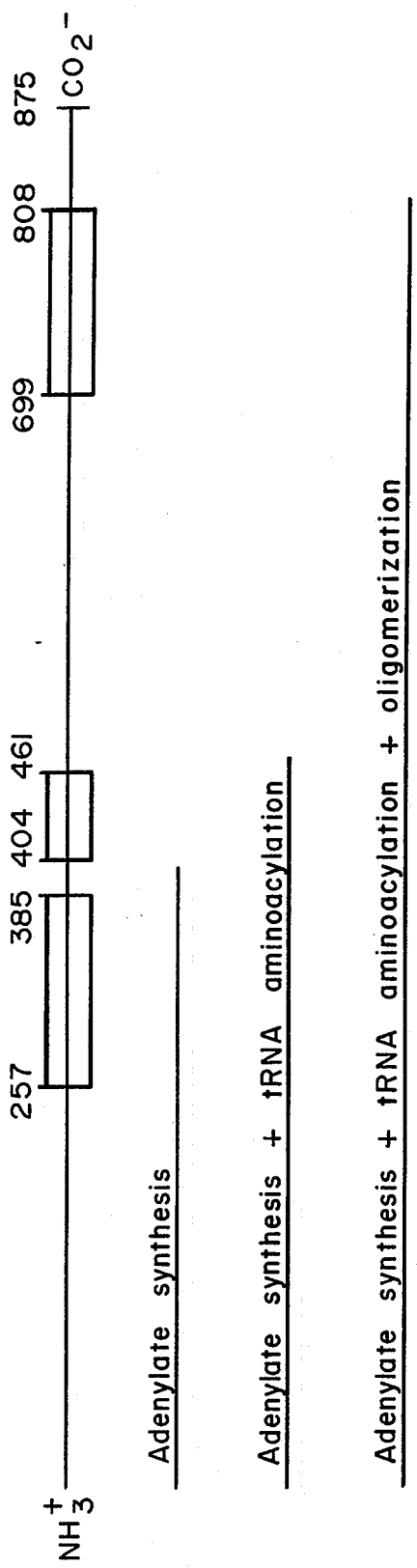

FIG. 4 graphs the regions essential for structure and function of Ala-tRNA synthetase. Shaded areas bracket the C-terminal boundaries of residues required for protein fragments with a specific function.

Figure 5A:
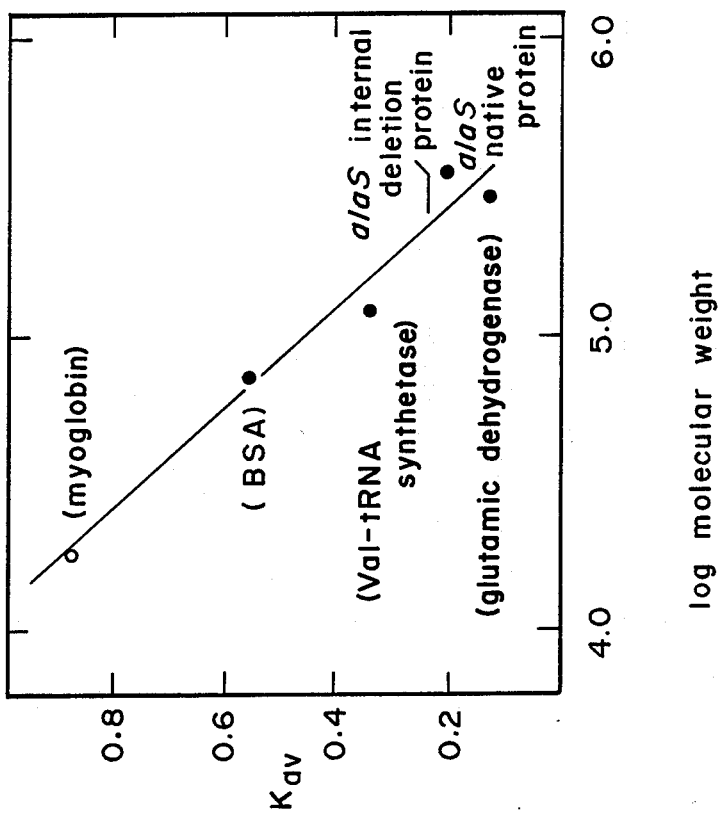

FIG. 5a charts the creation of an internal deletion in alaS which preserves the domain required for oligomerization.

Figure 5B:
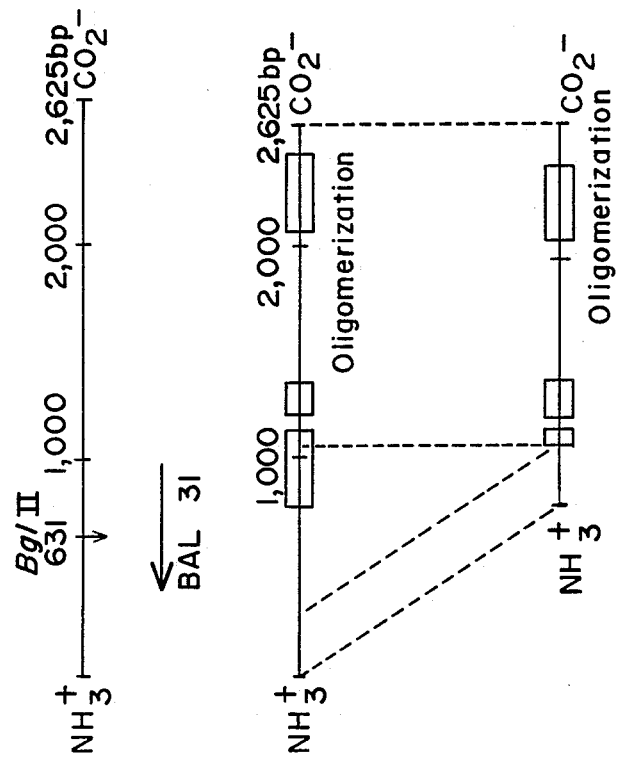

FIG. 5b charts the analysis of the alaS deletion protein. A protein extract was prepared from a 2.5-liter mid-log culture of SG4051 carrying the internal deletion plasmid. The plasmid-encoded proteins were preferentially labelled with 35S-methionine and the protein extract chromatographed using a G-200 gel-filtration column, with 20 mM potassium phosphate (pH 7.5), 50 mM sodium chloride, 1 mM phenylmethylsulphonylfluoride (PMSF) as column buffer. The column fractions were assayed for alaine- and valine-dependent PP$_i$ exchange activity to locate the chromosome encoded Val-tRNA synthetase and Ala-tRNA synthetase as internal molecular weight markers. The column was also calibrated using a series of protein standards, as shown. The data were plotted as log molecular weight versus $K_{av}$, where $K_{av} = (V_e - V_o)/(V_t - V_o)$ and $V_e$, $V_o$ and $V_t$ are the elution volume, void volume and total column volume, respectively. To locate the internal deletion protein, column fractions were dialysed against 1 mM PMSF in distilled water, lyophilized, resuspended in sample buffer and electrophoresed on 10% SDS polyacrylamide gelsl. The $^{35}$S-labelled, internal deletion protein was then visualized by autoradiography of these gels.

Figure 6:
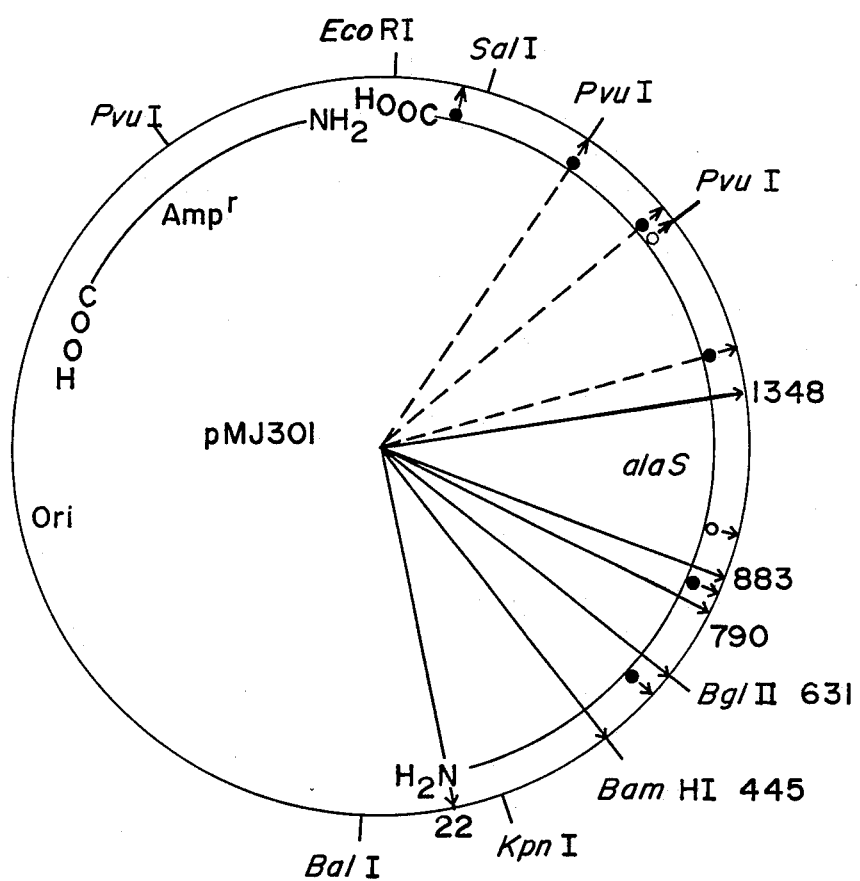

FIG. 6 shows the construction of plasmid deletions:
Plasmid pMJ301 was partially digested with Sau3A1, then cut to completion with BamHI. Two sets of plasmids resulted, one with the 5' deletion boundary at the Sau3A1 site at bp 22 and the other with the 5' deletion boundary at the BamHI site at bp 445. Base pairs are numbered with respect to the start of the alaS coding region. These sites are indicated by the dark solid line. The 3' deletion boundary exists at five sites, four of which leave the reading frame of the protein intact (light solid line) and the fifth which disrupts the reading frame (broken line).

FIG. 7 shows two autoradiograms showing maxicell analysis of plasmid encoded internal deletion proteins:

(a) Each plasmid is numbered according to the specific deletion which it encodes. Crude protein extracts from maxicell preparations were run on a 10% SDS polyacrylamide gel. The band at 30K shows the position of the Amp$^r$ protein present in all the lanes. The arrows indicate positions of alaS proteins.

(b) Maxicell analysis of two "double deletion" proteins along with proteins from parental plasmids. Arrows designate the positions of the alaS proteins.

Figure 8:
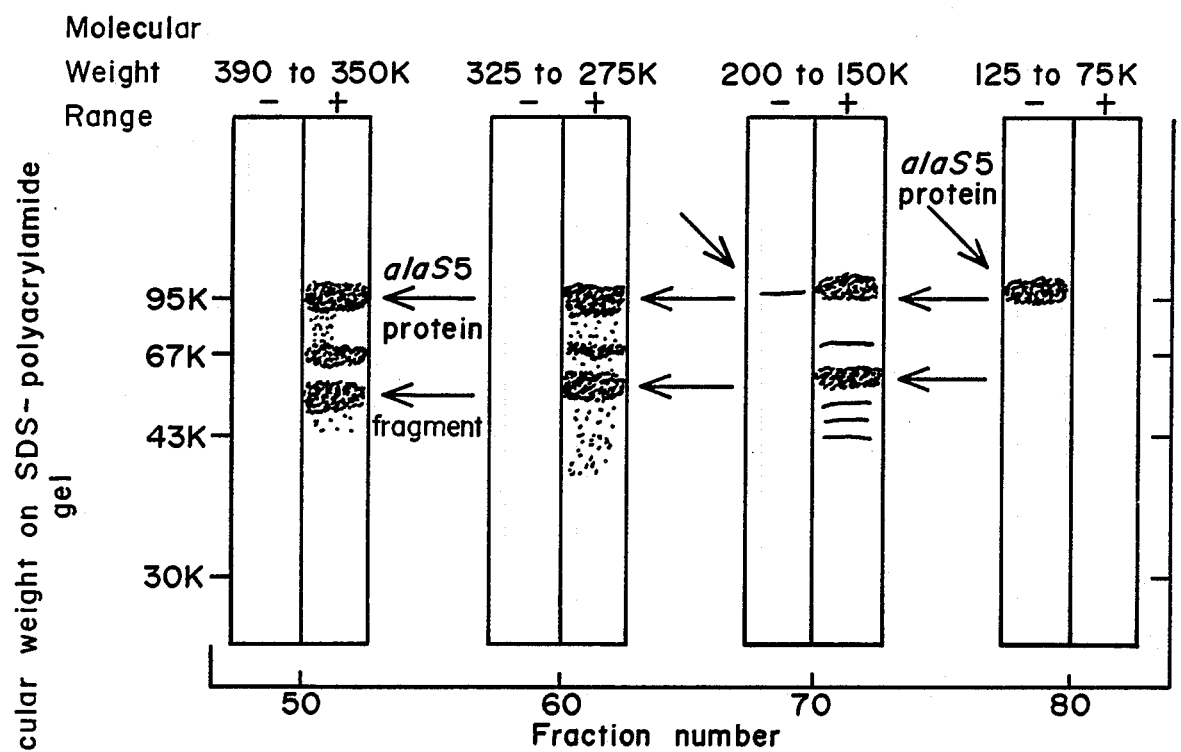

FIG. 8 is autoradiograms of the "Western Blots" of every tenth fraction from the gel filtration chromatography of extracts from alaS5 cells with (+) or without (−) the internal deletion plasmid with autoradiograms.

Figure 9:
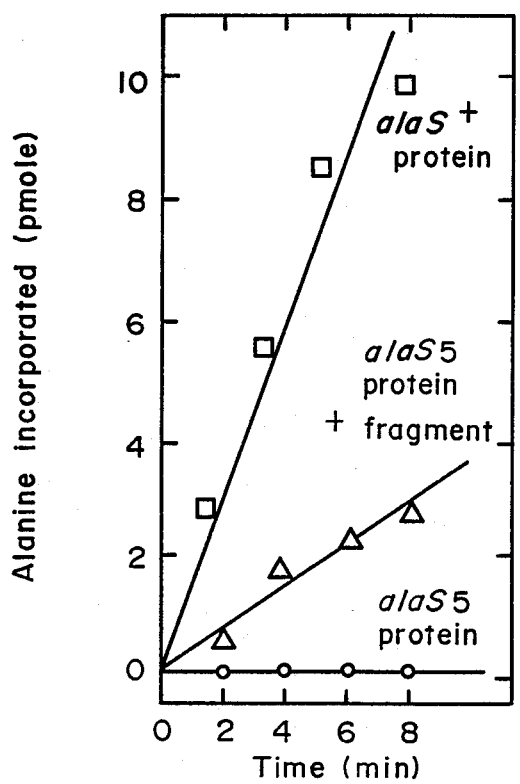

FIG. 9 graphs the aminoacylation activities of protein extracts from wild-type cells (alaS+), mutant cells (alaS5), and mutant cells with pMJ831 (alaS5 and fragment containing the oligomerization domain) with activities corrected for background alanine incorporation, and standardized to the alanine-dependent ATP-pyrophosphate exchange activity.

DETAILED DESCRIPTION OF THE INVENTION

In the present invention, the gene for the protein of interest is cloned. A nested set of overlapping deletions within the carboxyl terminal encoding portion is made. These deletions are made by partial restriction enzyme digestion, by the use of exonuclease III in conjunction with alpha-phosphorothioate nucleotides, or other available methods. The individual deletion constructions are made on recombinant DNA plasmids. These plasmids are transformed into the appropriate host strain and the production of the protein pieces investigated. If an *E. Coli* bacteria host is used, the synthesis of pieces can be visualized with a maxicell system. Those that are synthesized in sufficient amounts and are stable can be further investigated for biological activity. This can be done by in vitro assays, which test for a specific biological activity, or by in vivo complementation of defective phenotypes which require a specific biological activity. This approach is used to systematically map how much of a polypeptide, starting from the NH$_2$-terminus, is required for a specific biological activity and to delineate the region which is essential for the activity. For example, if two fragments differ in length by only x amino acids at their carboxyl termini, and the one which has the additional amino acids is active and the other is not, then those "x" amino acids are essential for the activity. In this way, functional units of a protein are delineated.

Examples of functional units or activities include sequences from enzymes involved in biosynthesis of cellular constituents and metabolites, such as nucleotides, nucleic acids, amino acids, cofactors, proteins, lipids, sugars and polysaccharides; hormones and receptors for hormones; antibodies; growth factors; peptide and protein regulatory molecules, and peptides and proteins of the immune system.

Once these functional units have been mapped by progressive carboxyl terminal deletions, then internal deletions may be introduced. These deletions remove internal parts of the protein and join together the flanking portions, in such a way as to join together flanking gene sections in the same reading frame, to give a new protein. The objective is to create new hybrid species where domains from different parts are juxtaposed together, or simply to eliminate large internal parts which are dispensible for the measured biological activity. In this way, a new set of protein pieces is created and defined.

To map the multiple functional domains in a protein or polypeptide sequence, the amino acid sequence is first determined either by amino acid sequencing of the polypeptide or by sequencing the nucleotides coding for the polypeptide. Next the "layout" of the functional parts of the polypeptide or protein are determined. At this point, pieces designated as "dispensable" or nonfunctional for the measured activity may be further characterized for activity such as oligomeric activity or protein to protein interactions at a site distant from the active site which somehow affects the functional domain.

The following example uses alanine-tRNA synthetase. This protein has at least three functions: adenylate synthesis, transfer RNA interactions, and oligomerization. Utilizing the method of the present invention, the gene coding for the protein is cloned into the BamHI site of a plasmid, pBR322, to produce a new plasmid, pMJ801. A "nested" set of truncated polypeptides, each beginning at the N-terminus and extending for various lengths to the C-terminus, are made by either digestion with restriction endonucleases or by removal of defined portions of the C-terminal coding region by partial restriction enzyme digestion, followed by ligation and insertion into the appropriate host strain.

In the first scheme, the plasmid is cut at the ClaI site and then treated with the Klenow fragment of DNA polymerase I in the presence of dATP (alpha S) to replace the 3'-terminal dAMP with dAMP (alpha S), making the DNA fragment inert to the action of exonuclease III. The side of the fragment adjacent to the protein coding region is reexposed by cleavage with HindIII and treated again with exonuclease III to produce an asymmetric digestion of just the carboxyl terminal part of the protein coding region of the fragment. Treatment with the S1 nuclease and Klenow fragment, in the presence of deoxynucleotide triphosphates, gives blunt ends which can be recirculized to produce plasmids with variable amounts of the protein gene with the C-terminal end removed. A marker on the plasmid, for example a gene for antibiotic resistance, is left intact to allow selection after transformation.

In the second scheme, fragments of increasing size are removed from the carboxyl coding region of the gene. The plasmid is first linearized by limited digestion with either MspI or TaqI, then the DNA is cut to completion at the unique ClaI site. Fragments with one to three kb deleted are recirculized with T4 DNA ligase. The plasmids are then transformed into the appropriate host strain and selected for the specific marker on the plasmid.

Variations as to which restriction enzymes and the specific order in which they are used would be determined for the individual gene to be re-configured. The cloned deleted genes are then synthesized in a protein system such as the maxicell system described by Sancar et al, *J. Bact.*, 137, 692–693 (1979), and the synthesized fragments which are synthesized are screened for the specific function of the cloned gene. For example, if the gene is for an essential protein, the plasmid may be transformed into a deficient host strain, and the host strain screened for viability or any other type of detectable phenotype following transformation. In the alternative, the deleted genes may be sequenced to determine the exact end of the deleted gene sequence, using restriction digestion. The molecular weights of the truncated proteins may also be determined, either by an autoradiogram of an SDS gel or by elution of an active fragment from a molecular seive column. Further functional assays may also be performed on the synthesized fragments.

The remaining portions of the gene which do not code for the functional activities may be further analyzed. For example, the polypeptide may be synthesized and examined for complementation with inactive functional polypeptides synthesized from deleted nucleotide sequences. In the following example using alanine-tRNA synthetase, adhesive or oligomeric pieces within the dispensible portions of the synthetase were found to be useful for altering the quaternary structure of an intact protein and for binding together two polypeptide fragments in which one contained an inactive functional domain and the other contained portions of the functional region and a region spatially remote from the functional region with oligomerization activity. The enzymatic activity of the inactive fragment was increased or restored due to alteration of the deficient enzymatic site by binding with the second polypeptide. These "adhesive" pieces with oligomerization activity acted independently of the other functional pieces.

Utilizing these methods for mapping, isolating, altering, and reassembling specific functional pieces of a protein, new proteins can be assembled. In particular, portions with functional activities may be reassembled into shorter proteins or proteins with a different quaternary structure or portions with defective functional sites may be restored by fusing onto the protein a specific "adhesive" or oligomeric piece or by complementation with a complementary piece which is bound to the defective protein by the specific "adhesive" piece.

This invention is further shown by the following non-limiting example using E. coli alanine-tRNA synthetase.

MAPPING OF FUNCTIONAL PIECES IN Ala-tRNA SYNTHETASE

Considerable variation in subunit size in quaternary structure is shown by individual members of the aminoacyl-tRNA synthetase class of enzymes. Quaternary structures which have been characterized include $alpha_1$, $alpha_2$, $alpha_2 beta_2$ and $alpha_4$. Subunit sizes range from approximately 330 amino acids for the Trp-tRNA synthetase to lengths of over 1,000 amino acids for the isoleucine and valine enzymes. The assignment of amino acids to nucleotide triplets is accomplished by aminoacyl tRNA synthetases. Each of the 20 enzymes catalyzes the same overall chemical reaction and is specific for one amino acid in the cognate set of tRNA isoacceptors. In spite of the common catalytic function, members of this class of enzymes have polypeptides that span a three to four fold range of lengths and have a diversity of quaternary structures. This contrasts with the immunoglobulins whose members have distinct antigen recognition specifities but little polypeptide size heterogeneity in the variable region.

A substantial part of the gene for a large synthetase can be deleted and, as long as the part which encodes the essential catalytic portion is retained, the resulting polypeptide fragment accurately aminoacylates tRNA in vivo. At least one aminoacyl-tRNA synthetase, alanine tRNA synthetase, an $alpha_4$ tetramer which is the largest of the known synthetases, has at least three different functional activities: adenylate synthesis (amino acid residues 257–385), transfer RNA interactions (amino acid residues 404–461), and oligomerization (amino acid residue 699–808).

Experiments were performed in E. coli Ala-tRNA synthetase. The entire 875 amino acid sequence was first determined by sequencing of the coding region of the gene and also by independently establishing the amino acid sequence of large sections of the polypeptide. Next, to determine the functional parts, the polypeptide was dissected into pieces and analyzed to find the smallest pieces which enable the enzyme to function in vivo and sustain protein synthesis. The part of the catalytic site required for synthesis of aminoacyl adenylate was also differentiated from the additional segment needed to attach the activated amino acid to tRNA. The segments of the polypeptide required for assembly of the protein into a tetramer, those with oligomerization activity, were also located.

FIG. 1a is a diagram of plasmid pMJ801. A segment of DNA containing the gene for alanine tRNA synthetase (alaS) was cloned into the BamHI site of pBR322. The direction of transcription and span of the coding region of alaS are indicated.

All deletions, performed on pMJ801, resulted in a nested set of truncated polypeptides. Each starts at the normal amino terminus and extends for different lengths towards the carboxyl terminus of the protein.

FIG. 1b is one scheme for production of deletions which remove variable amounts of the carboxyl terminal coding region. pMJ801 (2.5 microg) was digested with ClaI and then incubated with Klenow fragment (5 units BRL) in 25 microl. of 50 mM Tris-HCl pH 8.0, 5 mM $MgCl_2$, 10 mM beta-mercaptoethanol, and 0.1 mM dATP(alpha S). The incubation was at 22° C. for 3.5 h. The DNA was spermine precipitated and resuspended in 20 microl. of 6.6 mM Tris-HCl (pH 7.5), 6.6 mM $MgCl_2$, 6.6 mM beta-mercaptoethanol, and 50 mM NaCl. The DNA was digested with HindIII (New England Biolabs) and then treated for 2 h. at 22° C. with 25 units of exoIII (New England Biolabs); digestion was stopped by addition of 20 microl. of 2X S1 buffer (12 mM $ZnSO_4$, 0.3M NaCl, 1M NaOAC, and 95 units of BRL S1 nuclease). The S1 incubation went for 2 hrs. at 16° C. The exoIII and S1 nuclease reactions are essentially similar to that of Roberts and Lauer in *Methods Enzymology*, 68, 473–482 (1979). The reaction product was phenol and ether extracted and ethanol precipitated. The DNA was resuspended in 50 microl. of 50 mM Tris-HCl (pH 8.0), 5 mM $MgCl_2$, 10 mM beta-mercaptoethanol and 80 microM each of dATP, dCTP, dGTP, and dTTP. The reaction was incubated for 1.5 h. at 22° C. and the DNA spermine precipitated. The ligation was carried out in 35 microl. of 50 mM Tris HCl (pH 7.8), 10 mM $MgCl_2$, 20 mM DTT, 1 mM ATP, and 50 microg. BSA/ml with 400 units $T_4$ DNA ligase (New England Biolabs) for 30 h.

In this scheme, plasmid pMJ801 is cut at the ClaI site and then treated with the Klenow fragment of DNA polymerase I in the presence of dATP (alpha S). The combined action of the enzyme's exonuclease (in the 3' to 5' direction) and polymerase activities result in replacement of 3'-terminal dAMP with dAMP (alpha S). The replaced residue is encircled in FIG. 2a.

FIG. 1c shows a second scheme. The MspI partial digest (37° C. for 10 min) was with 60 microg. of pMJ801 in a 300 microl. reaction containing 10 mM Tris-HCl (pH 7.5), 10 mM MgCl$_2$, 1 mM beta-mercaptoethanol, 6 mM KCl, 100 microg. BSA/ml and 0.5 units MspI (New England Biolabs). The TaqI partial digest (37° C. for 5 min) was with 60 microg. pMJ801 in a 300 microl. reaction mixture containing 6 mM Tris-HCl (pH 7.5), 6 mM MgCl$_2$, 10 mM beta-mercaptoethanol, 6 mM NaCl, 100 microg. BSA/ml and 5 units TaqI (New England Biolabs). The partial digests were stopped by the addition of EDTA (pH 8.0) to a final concentration of 10 mM. After ethanol precipitation, both partial MspI and TaqI digests were cut to completion with ClaI. The ClaI digests were run on a 0.9% preparative agarose gel. Fragments between 4.7 and 7 kb were eluted from the agarose. Approximately 5 microg. of DNA was recovered from each digest. Ligation with T4 DNA ligase of 1.25 microg. MspI/ClaI or of TaqI/ClaI fragments was as described above in a 100 microl. reaction (4° C. for 12 h). After ethanol precipitation the ligated DNA was digested with HindIII.

With this strategy, fragments of increasing size are removed from the carboxyl terminal coding region. The plasmid is linearized by limited digestion with either MspI or TaqI; these enzymes have four base pair recognition sequences and therefore have multiple sites within the plasmid, but conditions were adjusted so that only one site per molecule was cut. After this limited digestion, the DNA was cut to completion at the unique ClaI site. Fragments with 1-3 kb deleted were recircularized with T4 DNA ligase.

The resulting plasmids were then transformed into *E. coli* with a selection for Amp$^r$ clones. In both schemes, the TAA stop codon of alaS is removed. However, stop codons are present in all three reading frames just beyond the ClaI site so that the number of residues added to the truncated terminus of Ala-tRNA synthetase is minimized (0-16 amino acids).

From the first scheme, 78 transformants were analyzed. One-third of the recombinant plasmids were found to be intermediate in size between pBR322 and pMJ801 and presumably are deleted in the alaS coding region. The remaining ones were either smaller than pBR322 or similar in size to pMJ801. Of those which were of the desired intermediate size, restriction digests established an approximate location of the deletion endpoints. These were found reasonably well distributed from the 3'-end to the 5'-end of the alaS coding region. Seven were selected for further analysis. These were sequenced by the dideoxy method of Sanger et al., *Proc. Natl. Acad. Sci. U.S.A.*, 74, 5463-5467 (1977) and Messing et al., *Nucleic Acids Res.*, 9, 309-321 (1981) across the deletion endpoint to determine the exact end of the alaS sequence and the number of in-frame pBR322 codons encountered before a stop.

From the second scheme, 40 recombinants were subjected to further investigation. Restriction digests on these recombinants established the location of the original MspI or TaqI site which was cut and ligated to the ClaI site. This in turn established the exact endpoint of the deletion and, from the known sequence of pBR322, the number of extraneous codons added before the first in-frame stop codon.

Production of proteins from the truncated alaS gene segments was investigated in maxicells where plasmid-encoded proteins are synthesized selectively in the presence of ($^{35}$S) methionine, as described by Sancar et al., *J. Bact.*, 137, 692-693 (1979). Crude extracts derived from maxicells containing the recombinant plasmids were run on SDS polyacrylamide gels and alaS protein fragment intensities were compared on an autoradiogram with that of the plasmid encoded beta-lactamase (responsible for Amp$^r$). Molecular weight standards were used to establish protein sizes. An autoradiogram of a gel containing some of these truncated proteins is shown in FIG. 2.

With approximately two-thirds of the recombinants, visualization was unequivocal and sizes of the plasmid encoded proteins on SDS gels were consistent with those established by determination of deletion endpoints. A summary is given in Table I. The amounts of protein fragments synthesized varied from quantities similar to that of the native protein to very little (amounts of native enzyme synthesized from the plasmid are about 10-fold above the levels made from the chromosomal gene). Small changes in the size of the alaS coding region can have a profound effect on protein levels.

Where possible, an enzymatic assay was also used to estimate amounts of alaS protein fragments. The alanine-dependent ATP-PPi isotope exchange assay of Calendar et al. in *Procedures in Nucleic Acid Research*, G. L. Cantoni and D. R. Davies, eds, pp. 384-399 (Harper and Row, N.Y. 1966) as described by Putney et al., *J. Biol. Chem.*, 256, 198-204 (1981was used with the fragments which can carry out the adenylate synthesis reaction as a sensitive measure of the amounts of alaS protein fragment. 2 mM alanine or valine was used in the reaction. Crude extracts were prepared from alumina ground cells (strain KL 380 containing a deletion plasmid) which were grown in LB medium to log phase ($A_{595}=1$). Protein concentrate was determined by the Bio-Rad Laboratories dye-binding method. 25 micrograms of protein was used in each 1 ml reaction.

For polypeptides with adenylate synthesis activity, those of 385 amino acids or more, levels of alanine-dependent ATP-PPi exchange were compared with that of the host strain. Activities were normalized by making use of the internal valine-dependent ATP-PPi exchange of the host strain. In cases where enhanced alanine-dependent exchange over background levels is observed, there generally is clear demonstration of an approximately proportional amount of protein-fragment synthesis on gel electrophoresis of the corresponding maxicell extracts.

A summary of the truncated proteins investigated and the presence or absence of adenylate synthesis activity measured in vitro is given in Table 1. Every protein fragment which includes or extends beyond residue 385 has adenylate synthesis activity, estimated to be within a factor of two of that of the native protein. Therefore, the adenylate synthesis section of the polypeptide (up to residue 385) is functionally independent of the rest of the chain.

An independent assay, such as the one described by A. Schrier and P. R. Schimmel in *Biochemistry*, 11, 1582-1589 (1972), can measure the overall aminoacylation of tRNA. This overall reaction is essential to maintain protein synthesis in vivo. Because Ala-tRNA synthetase is an essential protein, the ability of a truncated synthetase to sustain cell growth shows directly that it has catalytic sites for aminoacylation. For maximum sensitivity of testing for aminoacylation in vivo, a temperature-sensitive, conditional lethal host strain which has low levels of Ala-tRNa synthetase activity is used. Since only a small increment of aminoacylation activity by the truncated protein is necessary to achieve complementation, small specific activities contributed by the deletion polypeptides can be detected.

Tests for aminoacylation were done in the alaS5 background. This host grows well at 30° C., poorly at 37° C., and not at all at 42° C. Although synthesis of aminoacyl denylate by the alaS5 mutant protein appears normal, it has a substantially reduced specific activity for tRNA aminoacylation which is insufficient to maintain cell growth at the restrictive temperature. The mutation affects the oligomerization process so that the protein is a monomer. The use of a mutant allele which shows no subunit association in vitro decreases the possibility of complementation via hybrid interactions between deletion polypeptides and the mutant host protein. This possibility is further reduced for many of the deletion polypeptides because they have lost the domain for subunit association. Final confirmation of the main results was achieved by use of a specially-constructed alaS deletion strain which can only be maintained if the plasmid encoded truncated polypeptide alone aminoacylates in vivo.

Further confirmation of complementation was obtained by use of an alaS deletion mutant in which the gene has been removed from the chromosome (alaS 2). Cell growth is then only possible when recombinant plasmids are introduced which direct synthesis of polypeptides with sufficient Ala-tRNA synthetase activity.

In order for the fragment containing 461 residues to function in vivo, it must not only be fully functional for catalysis, but also must retain the specificity of aminoacylation. Whatever alterations in the chain are caused by the removal of over 400 carboxyl terminal residues, the remaining fragment has not been modified enough to sustantially alter its catalytic specificity.

The results in Table 1 show that residues between 257 and 385 are essential for adenylate synthesis. Residues between 385 and 461 are essential for interactions with tRNA to achieve aminoacylation. This segment is adjacent the sequence required for adenylate synthesis. During catalysis, the site for adenylate synthesis must come spatially close to the 3'-end of the tRNA where amino acid attachment occurs. However, there is a priori no requirement for these regions also to be juxtaposed in the sequence.

Ala-tRNA synthetase is an alpha$_4$ tetramer. The approximately 400 amino acid NH$_2$-terminal fragment obtained upon proteolysis is a monomer, suggesting that determinants in the chain for tetramer assembly are located in the carboxyl terminal half of the protein.

The capacity for oligomerization of some of the truncated proteins tabulated in Table 1 was tested by gel filtration chromatography under non-denaturing conditions. Results of chromatography on a Sephadex G-200 column are shown in FIG. 3. The column was calibrated with molecular weight standards. The native protein runs as a tetramer with a molecular weight of 380,000. The deletion containing 808 amino acids also runs as a tetramer on this column. However, the 699 amino acid protein and the amino terminal 468 amino acid fragment clearly run as monomers.

The results in FIG. 3 show that sites essential for tetramer assembly are contained between amino acids 699 and 808. It is also clear from the foregoing analysis that these residues are separated from those required for catalysis. Moreover, it appears that aminoacylation and maintenance of protein synthesis in vivo does not require tetramer assembly.

FIG. 4 summarizes in diagrammatic form the mapping results obtained. Three blocks of the polypeptide sequence shown to be essential for three of the functions of this synthetase are arranged in tandem along the enzyme sequence. This suggests that the gene may have been assembled in pieces, with different functional domains joined together to give the complete coding sequence. In view of these results, the core synthetase may be as small as 300–350 amino acids.

If the C-terminal piece is fused to the core enzyme to impart an additional function, then, at least to some degree, this C-terminal segment should function independently. This possibility was tested by creation of a large internal gene deletion in the section which encodes the catalytic domains, shown in FIG. 5a. The 2,625 nucleotide coding region was opened at the BglII site (nucleotide 631) and then partially digested with Bal31 nuclease, according to the method of H. B. Gray et al. in *Nucleic Acids Res.* 2, 1459–1467 (1975). From subsequent analyses, an internal deletion was isolated which joins codon 66 to codon 351, shown by DNA sequencing using the methods of Sanger et al in *Proc. Nat. Acad. Sci. U.S.A.*, 74, 5463–5467 (1977) and Messing et al. in *Nucleic Acids Res.* 9, 309–321 (1981), so that 285 internal amino acids have been removed. Examination of SDS-polyacrylamide gels of extracts, from maxicells containing this deletion construction, showed synthesis of the expected 65,000 MW polypeptide. Although catalytically inactive, confirmation that the polypeptide is the expected alaS internal deletion protein was obtained by precipitation by polyclonal antibodies directed against Ala-tRNA synthetase.

Gel filtration on a calibrated Sephadex G-200 column, shown in FIG. 5b, showed that the alaS internal deletion protein runs at a MW of 240,000, establishing that oligomerization occurs even with a major disruption of the amino-terminal half which contains the core enzyme.

Chemical crosslinking of the native Ala-tRNA synthetase tetramer, followed by denaturation and dissociation, shows the presence of dimers and tetramers in the crosslinked population. This argues for a subunit arrangement which generates 2-fold symmetry in the tetramer. The enzyme is known to repress its gene transcription in vitro by binding to an interrupted palindrome which flanks the gene's promoter site. This implies that a 2-fold axis in the protein fits onto that of the DNA. The oligomerization domain is therefore most probably associated with an additional function of this synthetase, that of gene regulation. This domain may in turn have been added on to that for the core enzyme, as is the case with the lac and the lambda repressors. These repressors have an amino terminal domain which binds to DNA and a carboxyl terminal oligomerization domain with a protease-sensitive connecting segment. The difference between these repressors and Ala-tRNA synthetase is that catalytic sites for aminoacylation of transfer RNA have been placed between the amino terminal and carboxyl terminal domains.

ANALYSIS OF FUNCTION OF "DISPENSABLE" SEQUENCES IN Ala-tRNA SYNTHETASE NOT REQUIRED FOR ADENYLATE SYNTHESIS OR tRNA INTERACTION

In view of the results suggesting that there may be coupling and integration of the dispensable parts, which may execute functions other than those associated with aminoacylation, with the indispensable or core components, further analysis and mapping studies were performed to determine whether or not the enzymes may be viewed simply as the sum of their component pieces. Coupling of the dispensable portions to the catalytic core is required if catalytic functions are integrated with other known properties, such as sequence specific DNA binding and gene regulation for synthesis of Ap4A.

An in vivo complementation scheme was designed. The activity of the catalytic core of the full length protein was measured, alone and when hybridized to a polypeptide piece containing the entire dispensable portion and an internal deletion in the catalytic core. The only active site in this hybrid of the full length alaS polypeptide bound to dispensable polypeptide is in the full length polypeptide.

The alaS5 mutant polypeptide is used as the full length chain because it is monomeric by virtue of a single point mutation that maps between codons 650 and 750. The activity of this alaS5 protein is reduced and is insufficient to sustain protein synthesis and cell growth at 42° C. Reactivation of the polypeptide was tested by in vivo complementation of the mutation by various inactive internal deletion fragments. The deletions were placed so as to destroy the catalytic sites. In vitro assays were also conducted.

The resected alaS gene fragments were also individually tested in a background (alaSΔ2) in which alaS is deleted from the chromosome. Because alaS is an essential gene, this test establishes whether the internal deletion fragments contain any residual catalytic activity. Utilizing the two systems, a differential complementation test was set up to screen for alaS gene fragments complementing alaS5 but not complementing alaSΔ2.

A family of deletions was created in which internal amino acid sequences were removed, with the flanking amino and carboxyl-terminal sequences joined together. Deletions were constructed by removal of specific internal alaS coding sequences from plasmid pMJ301. The construction of these plasmid deletions is shown in FIG. 6. The deletions remove variable portions from the region required for catalytic activity, but retain sequences in the carboxyl-terminal region. All together eight internal deletions of this type were constructed that preserved the proper reading frame. The deletions removed from 62 up to 442 amino acids.

Plasmid pMJ301 was constructed from a derivative of pMJ801 using the previously described exoIII/S1 nuclease digestion with the nuclease digestion stopped 10 nucleotides before reaching the alaS coding region. The nucleotide sequence is partially digested with BamHI to remove the BamHI site derived from pBR322, and then cut to completion with AvaI. The overhanging ends of the DNA fragments were filled in with the four deoxynucleotide triphosphates using the Klenow fragment of DNA polymerase I. This plasmid was designated pMJ301 and used for the subsequent plasmid constructions.

The alaS internal gene deletions were constructed from pMJ301. Approximately 70 microg. of plasmid DNA was cut with 2 U Sau3A1 for 10 min at 37° C. The DNA was then cut to completion with BamHI. The fragments were electrophoresed on a preparative agarose gel and fragments between 4.3 and 5.7 kb were isolated. They were subsequently recircularized with ligase and then cut with either KpnI or BglII prior to transformation.

Figure 7A:
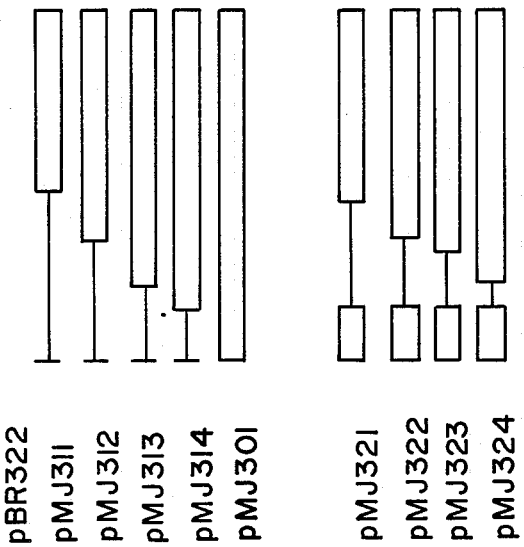
Figure 7A:
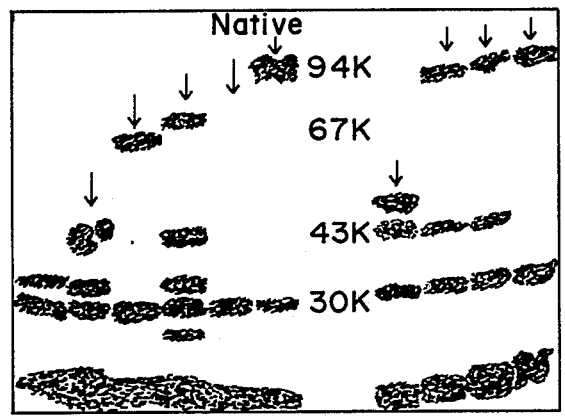
Figure 7B:
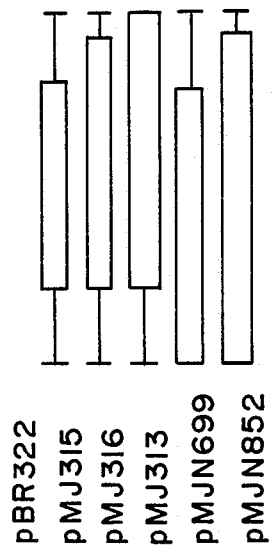
Figure 7B:
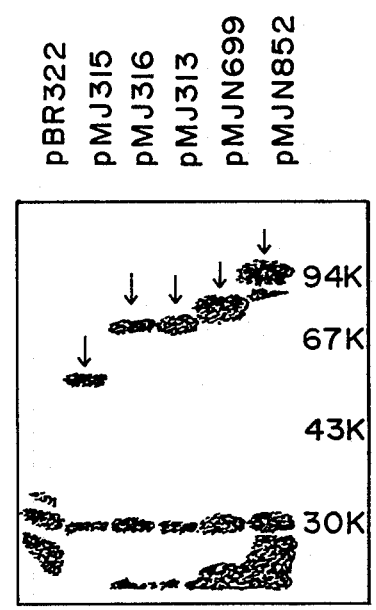

Synthesis in vivo of the eight proteins were studied in maxicells and analyzed for stability and sizes consistent with those expected based on the termination of the gene deletion endpoints. The results are shown in FIG. 7a.

Two "double deletions" were also created. These coupled an internal deletion in the catalytic portion with two C-terminal coding region deletions. The proteins encoded by these deletions were both visualized in maxicells, shown in FIG. 7b.

Recombinant plasmids containing the resected alaS gene fragments were transformed into an alaS5 or an alaSΔ2/pMJ901 background in which the chromosomal copy of alaS is deleted and the cell is maintained by pMJ901 which contains alaS in a temperature sensitive replicon. By virtue of this replicon, the plasmid is lost at 42° C. and the cells die unless rescued by a second plasmid encoding active alanine tRNA synthetase.

Table 2 shows a summary of the primary structures of 18 truncated polypeptides and their abilities to complement alaSΔ2 and alaS5. The polypeptides are arranged into three classes according to their complementation phenotypes. In group 1, there are three carboxyl-terminal deletions which complement neither mutant allele. These deletions extend well into the region of the synthetase required for catalytic activity.

There are four carboxyl terminal deletions that fall into group 2 and complement both mutant alleles. These are amino terminal fragments that range in size from slightly greater than half to almost full length protein. The first two of these cannot oligomerize, but all contain sites previously shown to be essential for catalytic activity.

The final class, group III, is comprised entirely of chains that have internal deletions which remove regions required for catalytic activity. None of these polypeptides complement alaSΔ2 but all of them complement alaS5. These nine constructions have retained the entire 400 amino acids beyond the amino terminal catalytic unit.

The two "double deletions" are shown separately. These contain an internal deletion in the catalytic portion joined to a truncated carboxyl terminal half. One of these ends at residue 699 and complements neither alaSΔ2 nor alaS5. The other extends to residue 852 and complements alaS5 but not alaSΔ2.

Protein extracts were prepared from the alaS5 strain and chromatographed on an Ultragel ACA34 (LKB) gel filtration column (1 cm×120 cm) in 10 mM NaH2PO4, pH 7.5, 0.5 mM pMSF. Individual 1.5 ml fractions were collected, concentrated, electrophoresed on SDS polyacrylamide gels, transferred electrophoretically from the gels to Genescreen (NEN), and the location of the alaS5 protein detected by probing the filter with $^{125}$I-labeled anti-Ala-tRNA synthetase antibodies. The procedure was also performed with protein extracts prepared from an alaS5 strain containing the previously described internal deletion plasmid, pMJ831, which retains sequences for the C-terminal half of the protein. Both the alaS5 protein and the C-terminal fragment were detected by the antibodies.

In the absence of the fragment synthesized from the internal deletion plasmid, the alaS5 protein runs on the gel filtration column in a size consistent with that found on SDS gels (95,000). The native protein runs at 380,000 on the gel filtration column. This is evidence that the alaS5 protein runs as a monomer. In the presence of the internally deleted fragment, the alaS5 protein is pulled into the higher molecular weight range of the gel filtration column where it is found to co-elute with the deletion polypeptide, suggesting that heterologous complexes are assembled with several of the possible permutations of stoichiometries of alaS5 protein and fragments. These results are shown in FIG. 8.

Protein extracts were prepared from strains carrying the alaS+ allele, the alaS5 allele, and the alaS5 allele containing internal deletion pMJ831. The protein concentrations were determined and in vitro alanine-dependent pyrophosphate exchange assays according to Calender and Berg, *Procedures in Nucleic Acid Research*, and aminoacylation assays according to Schreier and Schimmel, *Biochemistry*, 11, 1582–1589 (1972), were performed. The alaS5 protein has no detectable in vitro aminoacylation activity at either 30° C. or 42° C. In the presence of pMJ831, aminoacylation activity is about one third that of the alaS+ protein. The aminoacylation activities of the protein extracts are shown in FIG. 9. The in vitro effects correspond to activity at 30° C. Effects are not detectable in vitro at 42° C. probably because of protein instabilities at the higher temperature.

Of the set of deletions shown in Table 2, the largest N-terminal internal deletion (311) removes 442 amino acids and joins only the N-terminal 7 amino acids to the C-terminal half. The smallest internal deletion removes just 62 amino acids (149 to 210) from within the N-terminal part. These extremes, in each of the intermediate sized deletions, complement alaS5.

Complementation assays were performed by transforming bacterial strains KL380 as taught by Theall et al, in *Mol. Gen. Genet.*, 156, 221–227 (1977) and KL385 recAΔ1 Kan$^r$ alaSΔ2/pMJ901. Plasmid pMJ901 contains alaS fused into a vector carrying a temperature sensitive replicon described by Meacock and Cohen, in *Mol. Gen. Genetics*, 174, 134–147 (1979). Transformants were selected at 42° C. on LB ampicillin plates (50 microg./ml). KL385 recΔ1 Kan$^r$ alaSΔ2/pMJ901 was constructed by P1 transduction from a P1 lysate of JC7623 recΔ1 Kan$^r$ alaSΔ2/pMJ901 into cell strain KL385/pMJ901 as described by Theall et al (1977).

The complementation by C-terminal fragments of Ala-tRNA synthetase occurs by their formation of hybrids with the alaS5 protein. It is postulated that the mutation in the dispensable C-terminus is suppressed by hybrid formation, and that the effect is transmitted to the N-terminal catalytic core. There is no known precedence for this kind of complementation of enzyme activity.

Complementation of the defective alaS5 enzyme by fragments shown in Table 2 occurs regardless of the sizes or positional locations of the internal deletions in the N-terminal half. Each heterologous complex has, therefore, a different orientation of specific sequences in the N-terminal half of the alaS5 polypeptide with respect to the sequence counterparts in the deletion polypeptide. The implication is that the synthetase quaternary structure is assembled solely through interactions between oligomerization domains in the C-terminal moieties. Little or no contact is likely to occur between catalytic units. The tetrameric structure is probably organized around a two-fold axis. The complementation results are accomodated by a structure in which the C-terminal oligomerization domains are positioned against each other around that axis, leaving the catalytic cores more removed from the center of symmetry where they are free of interprotein contacts. This explains the ability of complexes to tolerate the diversity of arrangements occuring in the N-terminal halves.

As also shown in Table 2, two of the internal deletions have some C-terminal sequences removed as well. Complementation occurs with the double deletion in which the polypeptide extends to amino acid 852, but there is no complementation with the one that extends to residue 699, which is consistent with the previously noted importance of residue 699 to 808 for oligomerization of the synthetase. This is further evidence that complementation occurs through direct contacts between oligomerization domains in the fragment and in the alaS5 protein.

These results demonstrate that an enzyme is not just the sum of its pieces. The dispensable portion is integrated with a catalytic core by coupling the structure of the catalytic region to that of the dispensable parts, representing an efficient way to add additional domains to an aminoacyl tRNA synthetase without rebuilding the entire enzyme, thereby achieving a functionally integrated structure.

Although this invention has been described with reference to specific embodiments, it is understood that modifications and variations may occur to those skilled in the art. Such other embodiments and modifications are intended to fall within the scope of the appended claims.

What is claimed is:

1. A method for mapping and cloning nucleotide sequences that encode amino acid sequences having oligomeric or adhesive properties which can be used to impart greater stability to or restore or enhance the intrinsic activity of a protein molecule comprising:
   (a) cloning in a first plasmid a first nucleotide sequence encoding a first polypeptide, not including regulatory sequences, comprising an amino acid sequence with a first activity joined to an amino acid sequence with oligomeric activity, wherein oligomeric activity is defined as structure resulting in the assembly of a complex between the sequence with oligomeric activity and another polypeptide;
   (b) cloning in a second plasmid a second nucleotide sequence encoding a second polypeptide, not including regulatory sequences, wherein said second polypeptide comprises a portion of the amino acid sequences of said first polypeptide;
   (c) expressing said first and second nucleotide sequences cloned in steps (a) and (b) resulting in the synthesis of said first and second polypeptides;
   (d) permitting said first and second polypeptides synthesized from the nucleotide sequences cloned in steps (a) and (b) to combine;
   (e) screening the combined polypeptides for assembly of a complex between said first and second-polypeptides; and
   (f) measuring the activity of the complexed polypeptides of step (d) to determine if the polypeptide of step (b) has increased the activity of the polypeptide of step (a).

2. The method of claim 1 comprising further constructing said second nucleotide sequence to encode amino acid sequences of said first polypeptide with oligomeric activity.

3. The method of claim 2 further comprising locating said nucleotide sequence encoding amino acid sequences other than those for said first activity and amino acid sequences with oligomeric activity between said nucleotide sequences encoding said amino acid sequence with said first activity and the carboxyl-terminus of said polypeptide.

4. The method of claim 1 further comprising selecting said polypeptide having a first activity from the group of polypeptides having a measurable activity in the biosynthesis of cellular constituents, metabolites, nucleotides, amino acids, nucleic acids, cofactors, proteins, lipids, sugars, polysaccharides; polypeptides having a hormonal activity; polypeptides acting in growth regulation; and peptides and proteins regulating the immune response.

5. The method of claim 1 further comprising constructing a third recombinant plasmid comprising said nucleotide sequence encoding said amino acid sequence with oligomeric activity.

6. The method of claim 5 further comprising inserting said third plasmid into a host strain and synthesizing an amino acid sequence with oligomeric activity.

7. The method of claim 6 further comprising producing hybrid proteins comprising said amino acid sequence with oligomeric activity.

8. The method of claim 7 wherein said hybrid protein has enzymatic activity and is selected for enhanced intrinsic catalytic activity in comparison to the naturally occurring enzyme.

9. A method for producing a gene for a polypeptide with one or more intrinsic activities enhanced or stablized comprising:
   (a) inserting into a first plasmid a first nucleotide sequence encoding a first polypeptide with a first intrinsic activity, not including regulatory sequences, and
   (b) inserting into said plasmid a second nucleotide sequence, encoding a second amino acid sequence with oligomeric activity, wherein oligomeric activity is defined as structure resulting in the assembly of a complex between the sequence with oligomeric activity and another polypeptide, as a continuation of and in the same reading frame as the first nucleotide sequence, wherein said oligomeric activity enhances said first intrinsic activity.

10. The method of claim 9 further comprising inserting into said first plasmid additional nucleotide sequences for additional intrinsic activities that are a continuation of and in the same reading frame as said first nucleotide sequence.

11. The method of claim 9 further comprising selecting said nucleotide sequences from different sources.

12. A method for stablizing or enhancing one or more intrinsic activities in a polypeptide comprising:
   (a) cloning in a first plasmid a first nucleotide sequence, not including regulatory sequence, encoding a first polypeptide with a first intrinsic activity joined to an amino acid sequence with oligomeric activity, wherein oligomeric activity is defined as structure resulting in the assembly of a complex between the sequence with oligomeric activity and another polypeptide;
   (b) cloning in a second plasmid a second nucleotide sequence, not including regulatory sequences, encoding a second polypeptide, wherein said second polypeptide comprises said amino acid sequence of step (a) with oligomeric activity;
   (c) expressing said first and second nucleotide sequences resulting in the synthesis of said first and second polypeptides;
   (d) permitting the complex formation between said first and second polypeptides which results in enhancing one or more intrinsic activities in a polypeptide.

13. The method of claim 12 wherein said first polypeptide is selected from the group of naturally occurring polypeptides comprising an amino acid sequence for a first activity and an amino acid sequence with oligomeric activity.

14. The method of claim 12 wherein said first polypeptide is constructed by recombinant DNA techniques.

15. The method of claim 14 further comprising inserting nucleotide sequences encoding additional activities into said first plasmid that are a continuation of and in the same reading frame as said first nucleotide sequence.

16. The method of claim 15 further comprising inserting nucleotide sequences encoding additional amino acid sequences into said second plasmid that are a continuation of and in the same reading frame as said second nucleotide sequence.

* * * * *